United States Patent [19]

Wallquist

[11] Patent Number: 5,502,208
[45] Date of Patent: Mar. 26, 1996

[54] FINELY PARTICULATE CYANO-SUBSTITUTED DIKETOPYRROLOPYRROLE PIGMENTS AND THE PREPARATION THEREOF

[75] Inventor: Olof Wallquist, Marly, Switzerland

[73] Assignee: Ciba-Geigy Corporation, Tarrytown, N.Y.

[21] Appl. No.: 278,595

[22] Filed: Jul. 21, 1994

[30] Foreign Application Priority Data

Jul. 29, 1993 [CH] Switzerland .............................. 2298/93
May 18, 1994 [CH] Switzerland .............................. 1543/94

[51] Int. Cl.$^6$ .................... C07D 403/14; C07D 487/04; C09B 57/00; C08K 5/34
[52] U.S. Cl. .......................... 548/453; 524/92; 106/498
[58] Field of Search ............................................. 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,659,775 | 4/1987 | Pfenninger et al. | 524/92 |
| 4,720,305 | 1/1988 | Iqbal et al. | 106/288 Q |
| 4,931,566 | 6/1990 | Surber et al. | 548/454 |

*Primary Examiner*—David B. Springer
*Attorney, Agent, or Firm*—Michele A. Kovaleski

[57] ABSTRACT

Finely particulate 1,4-diketopyrrolo[3,4-c]pyrroles of formula

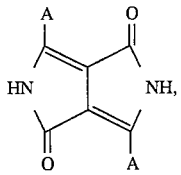

(I)

wherein A is a radical of formula

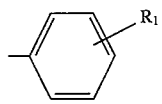

(II)

wherein $R_1$ is 3-CN, 4-CN or

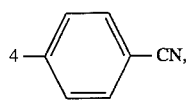

in which at least 84% of the pigment particles have a Stokes equivalent diameter of $\leq 0.40$ μm.

These pigments are distinguished by exceptional purity of shade, transparency, high gloss, good dispersibility and good rheology.

12 Claims, No Drawings

FINELY PARTICULATE CYANO-SUBSTITUTED DIKETOPYRROLOPYRROLE PIGMENTS AND THE PREPARATION THEREOF

The present invention relates to novel finely particulate cyano-substituted diketopyrrolopyrrole pigments which are characterised by a specific particle size distribution and which have exceptional purity of shade and transparency, high gloss, good dispersibility and good rheology, and to a process for the preparation thereof.

1,4-Diketopyrrolo-[3,4-c]-pyrrole pigments have been known for some years and are disclosed, inter alia, in U.S. Pat. No. 4,415,685 and 4,579,949. A number of these pigments have found acceptance as high-performance pigments. Recently the demand for highly transparent pigments forms, especially for obtaining metallic effect finishes, has increased appreciably. The problem has therefore also arisen of preparing a pure highly transparent form of even such highly regarded pigments, which form has good dispersibility and gloss as well as good rheology.

The preparation of 1,4-diketopyrrolo-[3,4-c]-pyrrole pigments by reacting a dialkyl succinate with a nitrile in the presence of a strong base and subsequently hydrolysing the resultant salt is disclosed in U.S. Pat. No. 4,579,949. It is stated that the hydrolysis shall preferably be carried out in water, an alcohol of 1 to 4 carbon atoms or, preferably, an acid, and that the more transparent pigment forms are obtained by carrying out the hydrolysis in the temperature range below 80° C. (by hydrolysis is meant here the conversion of the pigment alkali metal salts into the corresponding pigment, i.e. the protonation of the pigment alkali metal salts).

Processes for the preparation of special alkyl diketopyrrolopyrroles and asymmetrical diketopyrrolopyrroles starting from enamine diesters and pyrrolinones are disclosed in U.S. Pat. No. 4,659,775. According to this later publication, the hydrolysis is preferably carried out in water. Regarding the preparation of transparent forms, it is also recommended to carry out the hydrolysis in the temperature range below 80° C. The teaching of the later published U.S. Pat. No. 4,720,305 is similar and relates to the preparation of diketopyrrolopyrrole pigment mixtures from disuccinates and two different nitriles. According to this publication too, the hydrolysis is preferably carried out in water. To prepare more transparent forms, however, it is recommended to subject the pigment to subsequent comminution, conveniently by aqueous wet milling.

A process for the preparation of particularly pure pyrrolo-[3,4-c]-pyrroles, which comprises carrying out the hydrolysis sequentially in at least two steps, is disclosed in U.S. Pat. No. 4,931,566. The hydrolysis is carried out with an inorganic and/or organic acid, with water and alcohol or with an inorganic or organic acid, water and/or alcohol, preferably in the temperature range from 50° to 100° C. No mention is made of transparency. The products specifically mentioned are all opaque pigments.

It has now been found that, in the preparation of cyano-substituted diketopyrrolopyrroles, the special combination of three steps in the process and the subsequent conditioning, viz.

pouring the suspension of the pigment salt into water and/or an alcohol, the presence of an acid and pH<9 and, in particular, a temperature range above 90° C., yields finely particulate pigments in which at least 84% of the particles have a Stokes equivalent diameter (D 84) of ≦0.40 μm, and which have a surprisingly high purity of shade, transparency, gloss, good dispersibility and good rheology.

Accordingly, the invention relates to finely particulate 1,4-diketopyrrolo[3,4-c]pyrroles of formula

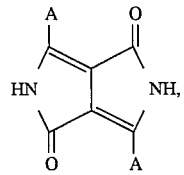

wherein A is a radical of formula

wherein $R_1$ is 3-CN, 4-CN or

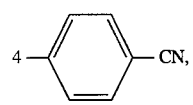

in which at least 84% of the particles have a Stokes equivalent diameter of ≦0.40 μm.

Preferred 1,4-diketopyrrolo[3,4-c]pyrroles of formula I are those in which at least 84% of the particles have a Stokes equivalent diameter of ≦0.30 μm.

The 1,4-diketopyrrolo[3,4-c]pyrrole of formula I, wherein $R_1$ is 3-CN and at least 84% of the particles have a Stokes equivalent diameter of ≦0.25 μm, is particularly preferred.

The invention further relates to the process for the preparation of the 1,4-diketopyrrolo-[3,4-c]pyrroles of formula I by reacting 1 mol of a dicyclohexyl, dialkyl, monoalkyl-monophenyl or diphenyl succinate, the alkyl moiety of the succinate radical being $C_1$–$C_{18}$alkyl and phenyl being unsubstituted or substituted by one or two halogen atoms, one or two $C_1$–$C_6$alkyl or $C_1$–$C_6$alkoxy groups, with 2 mol of a nitrile of formula $$A\text{—}CN \qquad (III)$$

wherein A is as defined above, in an inert organic solvent and in the presence of an alkali metal or of an alkali metal alcoholate as strong base, at elevated temperature, to give a pigment alkali metal salt, and subsequently generating a compound of formula I by protonation of the resultant pigment alkali metal salt and subsequent conditioning, which process comprises charging the suspension of the pigment alkali metal salt to water and/or an alcohol ROH, wherein R is $C_1$–$C_4$alkyl, in the presence of an acid in an amount sufficient to keep the pH at <9, and treating the mixture for 30 minutes to 24 hours at a temperature above 90° C.

$C_1$–$C_6$Alkyl is typically methyl, ethyl, n-propyl, isopropyl, n-butyl, tert-butyl, amyl, hexyl, decyl, dodecyl, tetradecyl or octadecyl. $C_1$–$C_6$Alkoxy is typically methoxy, ethoxy, n-propoxy, isopropoxy, butoxy or hexyloxy.

The acid can be added before or together with the suspension of the pigment salt.

It can be advantageous to use a buffer during protonation, conveniently a phosphate, acetate, citric acid or triethanolamine buffer.

R defined as $C_1$–$C_4$alkyl is typically methyl, ethyl, propyl, isopropyl, n-butyl, tert-butyl. Preferably R is methyl or ethyl.

The acids used as protonating agents are typically inorganic acids, including hydrochloric acid, phosphoric acid and, preferably sulfuric acid, or aliphatic or aromatic carboxylic or sulfonic acids, for example formic acid, acetic acid, propionic acid, butyric acid, hexanoic acid, oxalic acid, benzoic acid, phenylacetic acid, benzenesulfonic acid or p-toluenesulfonic acid or mixtures of these acids. Preferred organic acids are acetic acid and formic acid.

Protonation and conditioning are preferably carried out in the temperature range from 100° to 140° C. for 1 to 8 hours.

$R_1$ is preferably 3-CN,

The eligible dialkyl or diphenyl succinates may be symmetrical or asymmetrical diesters. It is preferred, however, to use symmetrical disuccinates, especially symmetrical dialkyl succinates. If a diphenyl or monophenylmonoalkyl succinate is used, phenyl may typically be unsubstituted or substituted by one or two halogen atoms, e.g. chlorine atoms, $C_1$–$C_6$alkyl groups, e.g. methyl, ethyl, isopropyl or tert-butyl, or $C_1$–$C_6$ alkoxy groups, e.g. methoxy or ethoxy. Phenyl is preferably unsubstituted phenyl. If a dialkyl succinate or monoalkylmonophenyl succinate is used, then alkyl may be unbranched or branched, preferably branched, and contain preferably 1 to 12, more particularly 1 to 8 and, most preferably, 1 to 5 carbon atoms. Branched alkyl is preferably sec- or tert-alkyl such as isopropyl, sec-butyl, tert-butyl and tert-amyl. It is most preferred to use symmetrical branched dialkyl succinates, wherein each alkyl moiety in the succinate radical contains 3 to 5 carbon atoms.

Illustrative examples of disuccinates are dimethyl, diethyl, dipropyl, dibutyl, dipentyl, dihexyl, diheptyl, dioctyl, diisopropyl, di-sec-butyl, di-tert-butyl, di-tert-amyl, bis[1,1-dimethylbutyl], bis[1,1,3,3-tetramethylbutyl], bis[1,1-dimethylpentyl], bis[1-methyl-1-ethylbutyl], bis[1,1-diethylpropyl], diphenyl, bis[4-methylphenyl], bis[2-methylphenyl], bis[4-chlorophenyl], bis[2,4-dichlorophenyl] and monoethylmonophenyl succinate.

The disuccinates listed above and the nitriles of formula III are known compounds and can be prepared by known methods.

The reaction of the disuccinate with the nitrile of formula III is carried out in an organic solvent. Suitable solvents are primary, secondary or tertiary alcohols of 1 to 10 carbon atoms such as methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol and 2,4,4-tfimethyl-2-pentanol; glycols such as ethylene glycol or diethylene glycol; also ethers such as tetrahydrofuran or dioxane, or glycol ethers such as ethylene glycol mono- or dimethyl ether, ethylene glycol mono- or diethyl ether, diethylene glycol monomethyl ether or diethylene glycol monoethyl ether, as well as dipolar aprotic solvents such as acetonitrile, benzonitrile, dimethyl formamide, N,N-dimethylacetamide, nitrobenzene and N-methylpyrrolidone, aliphatic or aromatic hydrocarbons such as benzene, or alkyl-, alkoxy- or halogen-substituted benzene such as toluene, xylenes, anisole or chlorobenzene; or aromatic N-heterocycles such as pyridine, picoline or quinoline. The above solvents can also be used as mixtures. It is expedient to use 5–20 parts by weight of solvent per 1 part by weight of reactant.

In the process of this invention it is preferred to use an alcohol as solvent, most preferably a secondary or tertiary alcohol. Preferred tertiary alcohols are tert-butanol and tert-amyl alcohol. Mixtures thereof or mixtures of these preferred solvents with aromatic hydrocarbons such as toluene or xylenes, or halogen-substituted benzenes such as chlorobenzene or o-dichlorobenzene, are of very particular interest.

Suitable strong bases in the process of this invention are alkali metals such as lithium, sodium and potassium, and alkali metal alcoholates that are preferably derived from primary, secondary or tertiary aliphatic alcohols of 1 to 10 carbon atoms, e.g. lithium, sodium or potassium methylate, ethylate, n-propylate, isopropylate, n-butylate, sec-butylate, tert-butylate, 2-methyl-2-butylate, 2-methyl-2-pentylate, 3-methyl-3-pentylate and 3-ethyl-3-pentylate. It is, however, also possible to use a mixture of these alkali metal alcoholates. It is preferred to use alkali metal alcoholates, the alkali preferably being sodium or potassium, and the alcoholate preferably being derived from a secondary or tertiary alcohol. Particularly preferred strong bases are therefore typically sodium or potassium isopropylate, sec-butylate, tert-butylate and tert-amylate. The alkali metal alcoholates can also be prepared in situ by reacting the appropriate alcohol with the alkali metal.

The strong base may be used in the process of this invention typically in an amount of 0.1 to 10 mol, preferably 1.9 to 4.0 mol, based on 1 mol of disuccinate. Although stoichiometric amounts of base in principle suffice, an excess of base will often have a beneficial influence on the yield.

The reaction may conveniently be carried out in the temperature range from 60° to 140° C., but preferably from 80° to 120° C.

For the reaction of the disuccinate with the nitrile or nitriles of formulae III it is in principle possible to add all the components together at low temperature and then to heat the mixture in the range of the reaction temperature, or to add the individual components, in any order, in the range of the reaction temperature. A preferred embodiment of the reaction, which usually has a particularly beneficial influence on the yield, comprises adding the nitrile to be reacted together with the base to the reactor and then adding the disuccinate in the range of the reaction temperature. A further possible procedure comprises adding disuccinate and the nitrile to be reacted simultaneously to the base. It is entirely possible to carry out the reaction not only batchwise, but also continuously.

Especially when using disuccinates containing lower alkyl groups, and alcoholates derived from lower alcohols such as methanol, ethanol, n-propanol, isopropanol or tert-butanol, it can be advantageous to remove the lower alcohol formed during the reaction continuously from the reaction medium in order to obtain higher yields.

If the solvent is an alcohol and the base is an alcoholate, then it can be useful to choose an alcohol and an alcoholate containing identical alkyl groups. It can likewise be useful if in addition the disuccinate contains such alkyl groups.

For the protonation of the pigment salt, it is possible either to add the pigment alkali metal salt to the protonating agent consisting of water and/or alcohol and the acid, or to add the pigment alkali metal salt and the acid simultaneously to the water and/or alcohol. The water and/or alcohol may be used in any mixture ratios from 5 to 20 parts by weight per 1 part of the pigment alkali metal salt. The acid is conveniently used in an amount of 0.5 to 3 equivalents, based on the base, but at all events in an amount such that the pH is <9 when the protonation is complete.

The compounds of formula I may be used as pigments for organic materials of high molecular weight. The pigments can usually be used direct in the pigment form in which they are obtained after the inventive process. Depending on the end use requirement and if necessary, their crystal morphology can subsequently be further optimised by one of the numerous conventional aftertreatments.

Depending on the end use requirement it can be advantageous to prepare mixtures of compounds of formula I. This can be done by mixing different reaction solutions which have been prepared independently of one another before protonation, protonising them together and then isolating the resultant product.

Organic materials of high molecular weight that can be coloured or pigmented with the compounds of formula I typically include cellulose ethers and esters such as ethyl cellulose, nitrocellulose, cellulose acetate and cellulose butyrate, natural and synthetic resins such as polymerisation or condensation resins, e.g. aminoplasts, especially urea and melamine/formaldehyde resins, alkyd resins, phenolic plastics, polycarbonates, polyolefins such as polyethylene and polypropylene, polystyrene, polyvinyl chloride, polyacrylonitrile, polyacrylates, polyamides, polyurethanes, polyesters, rubber, casein, silicon and silicon resins, singly or in mixtures.

It is immaterial whether the above high molecular weight organic compounds are in the form of plastic materials, melts or in the form of spinning solutions, coating materials, paint systems or printing inks. Depending on the envisaged end use it can be advantageous to use the compounds of formula I as toners or in the form of preparations. Based on the organic material of high molecular weight to be pigmented, the compounds of formula I can be used in an amount of 0.01 to 30% by weight, preferably of 0.1 to 10% by weight.

Depending on the conditioning method or utility, it can be advantageous to add specific amounts of texture improvers to the pigments before or after conditioning, provided such addition does not have an adverse effect when using the pigment compositions of the invention (especially in polyethylene). Particularly suitable texture improvers are fatty acids containing at least 18 carbon atoms, typically stearic or behenic acid or the amides or metal salts thereof, preferably magnesium salts, as well as plasticisers, waxes, resin acids such as abietic acid, rosin soap, alkylphenols or aliphatic alcohols such as stearyl alcohol or aliphatic 1,2-dihydroxy compounds of 8 to 22 carbon atoms, e.g. 1,2-dodecanediol, and also modified rosin maleate resins or fumaric acid rosin resins. The texture improvers are preferably added in amounts of 1.0 to 50% by weight, most preferably 5 to 40% by weight, based on the final product. The 1,2-dihydroxy compounds referred to above, preferably 1,2-dodecanediol, also serve to enhance the filterability of the suspended pigment composition.

The colorations obtained, typically example in plastics, fibres, paint systems or printing inks, are distinguished by high purity of hue, superior colour strength, high transparency, good fastness to oversparying, migration, heat, light and weathering, as well as by good gloss.

The compounds of formula I axe distinguished, as already mentioned, very particularly by exceptional purity of shade, high transparency, good dispersibility, good rheology and by superior gloss of the colorations obtained therewith. Accordingly, the preferred utility is for colouring plastics, water- and/or solvent-based paint systems, especially automotive lacquers or printing inks. The particularly preferred utility is for coloring printing inks.

The invention is illustrated by the following Examples in which, unless otherwise indicated, parts and percentages are by weight.

EXAMPLE 1

1150 ml of tert-amyl alcohol are charged to a sulfonation flask under nitrogen. After the addition of 38.4 g of sodium, the mixture is heated to 95°–102° C. The fused sodium is then vigorously stirred overnight at 100°–105° C. The solution is cooled to 85° C., 145.6 g of 3-cyanobenzonitrile are added, the batch is washed with 30 ml of tert-amyl alcohol and then 127.8 g of diisopropyl succinate are added dropwise over 2 hours at 80°–85° C. The reaction mixture is stirred for 4 hours at this temperature and afterwards poured into a mixture of 462 ml of water, 1738 ml of methanol and 190.3 g of concentrated hydrochloric acid. The batch is stirred at 130° C. for 6 hours (pH<7), cooled, filtered, and the filter product is washed with methanol/water and once more with water. The resultant pigment is dried at 80° C. in a vacuum drying oven, giving 168.5 g of an orange powder which colours PVC in a pure, transparent orange shade.

| Analysis: | C | H | N |
|---|---|---|---|
| calcd: | 71.00% | 2.98% | 16.56% |
| found: | 70.01% | 3.08% | 16.42% |

EXAMPLE 2

The procedure of Example 1 is repeated, replacing the mixture of methanol/water/hydrochloric acid with 2560 ml of water and 83.0 g of 96% sulfuric acid and, after stirring for 6 hours at 140° C., carrying out steam distillation. After filtration and washing and drying the filter product, there are obtained 178.9 g of an orange powder that colours PVC in a pure, transparent orange shade.

| Analysis: | C | H | N |
|---|---|---|---|
| calcd: | 71.00% | 2.98% | 16.56% |
| found: | 70.50% | 3.15% | 16.16% |

EXAMPLE 3

700 ml of tert-amyl alcohol are charged to a sulfonation flask under nitrogen and heated to 80° C. Then 24.2 g of sodium are added and the mixture is heated to c. 95°–110° C. The fused sodium is vigorously stirred overnight at 100°–110° C. After cooling to 80° C., 89,7 g of 3-cyanobenzonitrile are added and then 80.9 g of diisopropyl succinate are added dropwise over 2 hours and the reaction mixture is stirred overnight at the same temperature. Then the reaction mixture together with 60 % sulfuric acid is added over c. 3 hours to a refluxing mixture of 600 ml of water, 600 ml of methanol and 8.2 g of sodium dihydrogen phosphate. The sulfuric acid is added dropwise to the reaction mixture in an amount sufficient to keep a pH range of 6–8. The mixture is refluxed for 4 hours and thereafter stirred for 6 hours at 100° C., then cooled and filtered. The residue is washed with methanol/water and once more with water and dried at 80° C. in a vacuum drying oven, giving 104.4 g of an orange powder that colours PVC in a pure, transparent orange shade.

| Analysis: | C | H | N |
|---|---|---|---|
| calcd: | 71.00% | 2.98% | 16.56% |
| found: | 68.80% | 3.07% | 16.01% |

EXAMPLE 4

160 ml of tert-amyl alcohol are charged to a sulfonation flask under nitrogen. Then 6.9 g of sodium are added and the mixture is heated to c. 98°–108° C. and the fused sodium is vigorously stirred overnight at 100°–105° C. After cooling to 80° C., 25.6 g of 4-cyanobenzonitrile are added, followed by the dropwise addition of 22.2 g of diisopropyl succinate over 2 hours at the same temperature. The reaction mixture is thereafter stirred for 22 hours at 80° C. and subsequently poured into a mixture of 30.5 ml of 36% hydrochloric acid, 345 ml of methanol and 115 ml of water. The batch is stirred for 6 hours at 130° C., filtered, and the filter residue is washed with methanol and water and dried in a vacuum drying oven at 80° C., giving 32.4 g of a readily dispersible dark powder that colours PVC in a dark red transparent shade.

| Analysis: | C | H | N |
|---|---|---|---|
| calcd: | 71.00% | 2.98% | 16.58% |
| found: | 69.59% | 3.05% | 16.20% |

EXAMPLE 5

Example 5: 5 g of the pigment of Example 1, 56.56 g of alkyd resin ®ALKYDAL F310 (Bayer), 60% in xylene, 21.70 g of xylene, 0.94 g of silicone oil (1% in xylene) and 13.55 g of melamine resin ®CYMEL 327 (Cyanamid), 90% in isobutanol, are dispersed together in a disperser (®Skandex-Disperser BA-520, in analogy to DIN 53 238, part 10) until step 6 (DIN 53 238, part 24) is attained. After dilution, the mass-tone varnish so obtained can be used to determine the particle size distribution by photosedimentometry (cf. Herbst & Hunger, Industrielle organische Pigmente, VCH 1987, pp. 32–34 and 40–43 and K. Brugger, Powder Technology 13, 215–221 (1976)). In this Example, at least 84% by weight of the pigment particles have a Stokes equivalent diameter of ≦0.25 μm.

The mass tone varnish can also be applied with a spiral applicator (100 μm wet film) to a transparent polyethylene film. The varnish is then allowed to dry in the air for 15 minutes at room temperature and then stoved for 30 minutes at 115° C.

EXAMPLE 6

7.5 g of the pigment of Example 1, 98.9 g of a CAB solution consisting of

| | |
|---|---|
| 41.0 g | of cellulose acetobutyrate ®CAB 531.1, 20% in butanol/xylene 2:1 (Eastman Chem.) |
| 1.5 g | of zirconium octoate, |
| 18.5 g | of ®SOLVESSO 150 (ESSO) (aromatic hydrocarbons), |
| 21.5 g | of butyl acetate and |
| 17.5 g | of xylene, |

36.5 g of polyester resin ®DYNAPOL H700 (Dynamit Nobel), 4.6 g of melamine resin MAPRENAL MF650 (Hoechst) and 2.5 g of dispersant ®DISPERBYK 160 (Byk Chemie) are dispersed together for 90 minutes in a disperser (total varnish: 150 g; 5% of pigment).

For the base coat layer, 27.69 g of the mass tone varnish so obtained are mixed with 17.31 g of Al stock solution (8%) consisting of

| | |
|---|---|
| 12.65 g | of ®SILBERLINE SS 3334AR, 60% (Silberline Ltd.) |
| 56.33 g | of CAB solution (composition as above) |
| 20.81 g | of polyester resin ®DYNAPOL H700 |

| | |
|---|---|
| 2.60 g | of melamine resin ®MAPRENAL MF650 |
| 7.59 g | of ®SOLVESSO 150 | and the mixture is sprayed on to an aluminium sheet (wet film c. 20 μm). After drying in the air for 30 minutes at room temperature, a TSA varnish consisting of

| | |
|---|---|
| 29.60 g | of acrylic resin ®URACRON 2263 XB, 50% in xylene/butanol (Chem. Fabrik Schweizerhalle), |
| 5.80 g | of melamine resin ®CYMEL 327, 90% in isobutanol, |
| 2.75 g | of butyl glycol acetate, |
| 5.70 g | of xylene, |
| 1.65 g | of n-butanol |
| 0.50 g | of silicone oil, 1% in xylene, |
| 3.00 g | of light stabiliser ®TINUVIN 900, 10% in xylene (Ciba) |
| 1.00 g | of light stabiliser ®TINUVIN 292, 10% in xylene (Ciba) | is spray applied as top coat finish (wet film c. 50 μm). The varnish is allowed to dry in the air for 30 minutes at room temperature, and then stoved for 30 minutes at 130° C.

EXAMPLE 7

Preparation of a gravure/flexographic printing ink.

| | |
|---|---|
| 15 g | of the pigment of Example 1, |
| 20 g | of a clear varnish consisting of |
| | 20 g of nitrocellulose type A |
| | 4 g of dioctyl phthalate |
| | 56 g of ethanol and |
| | 20 g of ethyl acetate |
| | and |
| 25 g | of ethanol | are dispersed with a dissolver at 15 m/s over 30 minutes.

To the batch are then added 40 g of the above clear varnish and the mixture is dispersed for 5 minutes with the dissolver. This milling stock is fed into a bead mill by means of a pump with coarse filtration and finely dispersed therein. Exceptional transparency/gloss properties are obtained with this printing ink in gravure/flexographic printing as well as in offset printing.

What is claimed is:

1. A finely particulate 1,4-diketopyrrolo[3,4-c]pyrrole of formula

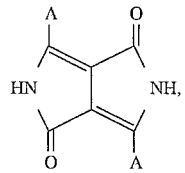

(I)

wherein A is a radical of formula

(II)

wherein $R_1$ is 3-CN, 4-CN or

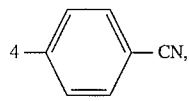

in which at least 84% of the pigment particles have a Stokes equivalent diameter of ≦0.40 μm.

2. A 1,4-diketopyrrolo[3,4-c]pyrrole of formula I according to claim 1, in which at least 84% of the pigment particles have a Stokes equivalent diameter of ≦0.30 μm.

3. A 1,4-diketopyrrolo[3,4-c]pyrrole of formula I according to claim 1, wherein $R_1$ is 3-CN and at least 84% of the pigment particles have a Stokes equivalent diameter of ≦0.25 μm.

4. A process for the preparation of a 1,4-diketopyrrolo[3,4-c]pyrrole of formula I according to claim 1, which process comprises reacting in a molar ratio one mol of a dicyclohexyl, dialkyl, monoalkylmonophenyl or diphenyl succinate, the alkyl moiety of the succinate radical being $C_1$–$C_{18}$alkyl and phenyl being unsubstituted or substituted by one or two halogen atoms, one or two $C_1$–$C_6$alkyl or $C_1$–$C_6$alkoxy groups, with two mol of a nitdie of formula

A—CN  (III)

wherein A is as defined in claim 1, in an inert solvent and in the presence of an alkali metal or of an alkali metal alcoholate as strong base, at a temperature of from 60° to 140° C., to give a suspension in the inert organic solvent of a pigment alkali metal salt of the formula

and subsequently generating a compound of formula (I) according to claim 1 by protonation of said pigment alkali metal salt and subsequent conditioning, wherein said protonation of the pigment alkali metal salt and subsequent conditioning comprise charging the suspension of the pigment alkali metal salt to water and/or an alcohol ROH, wherein R is $C_1$–$C_4$ alkyl, in the presence of an acid in an amount sufficient to keep the pH of less than 9, and treating the mixture for 30 minutes to 24 hours at a temperature of above 90° C.

5. A process according to claim 4, wherein $R_1$ in formula II is 3-CN.

6. A process according to claim 4, wherein the alcohol is methanol or ethanol.

7. A process according to claim 4, wherein an inorganic acid selected from the group consisting of hydrochloric acid, sulfuric acid and phosphoric acid is used for the protonation.

8. A process according to claim 4, wherein an aliphatic or aromatic carboxylic or sulfonic acid selected from the group consisting of formic acid, acetic acid, propionic acid, butyric acid, hexanoic acid, oxalic acid, benzoic acid, phenylacetic acid, benzenesulfonic acid and p-toluenesulfonic acid is used for the protonation.

9. A process according to claim 7, wherein sulfuric acid is used.

10. A process according to claim 8, wherein acetic acid or formic acid is used.

11. A process according to claim 4, wherein the protonating agent is used in any mixture ratio from 5 to 20 parts by weight of protonating agent per 1 part of pigment alkali metal salt.

12. A process according to claim 4, wherein protonation and conditioning are carried out in the temperature range from 100° to 140° C.

* * * * *